United States Patent [19]
Russell et al.

[11] Patent Number: 5,232,452
[45] Date of Patent: Aug. 3, 1993

[54] RADIOLOGY MARKER SYSTEM AND DISPENSER

[75] Inventors: Donald G. Russell, Kensington; Gail Burns, Torrington, both of Conn.

[73] Assignee: Beekley Corporation, Bristol, Conn.

[21] Appl. No.: 809,279

[22] Filed: Dec. 13, 1991

[51] Int. Cl.$^5$ .............................................. A61B 17/00
[52] U.S. Cl. .................................... 604/180; 378/163
[58] Field of Search ............... 378/162, 163, 164, 165, 378/63; 424/2, 4; 604/174, 180; 128/653.4, 637, 653.1

[56] References Cited

U.S. PATENT DOCUMENTS

| | | | |
|---|---|---|---|
| 3,171,959 | 3/1965 | Kozek et al. | 378/164 |
| 3,547,121 | 12/1970 | Cherry | 378/164 X |
| 4,339,035 | 7/1982 | Marcus et al. | 206/370 |
| 4,506,676 | 3/1985 | Duska | 378/162 X |
| 4,860,331 | 8/1989 | Williams et al. | 606/130 X |

OTHER PUBLICATIONS

X-Rite Radio Opaque Label Tape, X-Ray Identification Corp., no date, Brochure.

Primary Examiner—Robert A. Hafer
Assistant Examiner—Sam Rimell
Attorney, Agent, or Firm—Chilton, Alix & Van Kirk

[57] ABSTRACT

A marker system for use in radiography. The marker system includes an elongated base tape, a bendable, fabric covered wire containing a material that is opaque to imaging radiation, such as lead, and a continuous row of adhesive pads fixedly aligned along the wire. The adhesive pads are releasably adhered to the base tape and are manually removable from the base tape together with the wire for releasable adherence to a subject The marker system is dispensed in a convenient handy dispensing package which holds a roll of the marker system and ejects a line of wire with markers attached thereto as the base tape is pulled. Wire clippers are attached to the dispenser for cutting the markers.

20 Claims, 2 Drawing Sheets

RADIOLOGY MARKER SYSTEM AND DISPENSER

BACKGROUND AND SUMMARY OF THE INVENTION

When imaging various parts of the human body, it has been the practice of the physician or technologist to mark certain body parts with a thin lead strip or wire which can be seen on the radiographic image that is obtained. One purpose of identifying particular portions of the body is to prevent the physician who examines the image from being misled by artefactual shadows cast by certain body tissues of varying radiographic density. For example, it is known to use lead nipple markers described in U.S. Pat. No. 4,339,035, Marcus et al. Another purpose of identification is to delineate the margins of the radiation field which will be the target of radiation therapy. For this purpose it is known to tape paper clips or pieces of lead to a patient's body in order to mark a particular region or body part. This marking process can be uncomfortable for the patient and inconvenient for the physician or technician, and may be inaccurate.

An object of the invention is to provide a convenient and effective marker system for use in radiology.

Another object of the invention is to provide a marker system for use in radiology which is safe and comfortable for the patient.

Yet another object of the invention is to provide a disposable radiology marker system of the type described above which is relatively inexpensive to manufacture.

In addition, the invention provides for prevention of the spread of infection by permitting and encouraging single patient use.

A further object of the invention is to provide a radiology marker system that comes in a convenient and accessible dispenser.

Yet another object of the invention is to provide a marker system for use in radiology in which an adhesive marker having a lead-containing wire of a desired length can be conveniently cut.

Other objects will be in part obvious and in part pointed out more in detail hereinafter.

The invention in a preferred form is a marker system for use in radiology. The marker system comprises an elongated base tape, a bendable, covered wire containing a material that is opaque to imaging radiation, and a plurality of adhesive support pads mounted along the length of the wire. The adhesive pads are releasably adhered to the base tape and are manually removable from the base tape together with the wire for releasable adherence to a subject.

Another embodiment of the invention is a dispenser containing the marker system of the invention. The dispenser includes a package for holding and supplying the tape, an elongated base tape disposed in the package and dispensable therefrom, a bendable, fabric covered wire comprising a material that is opaque to imaging radiation, and a plurality of adhesive members fixedly aligned along the length of the wire in a continuous arrangement, as discussed above. Preferably, the dispenser further includes a cutting device for cutting the marker to a desired length.

The invention accordingly consists in the features of construction, combination of elements and arrangement of parts which will be exemplified in the construction hereafter set forth and the scope of the application which will be indicated in the appended claims.

DETAILED DESCRIPTION OF THE PREFERRED EMBODIMENTS

Figure 1:
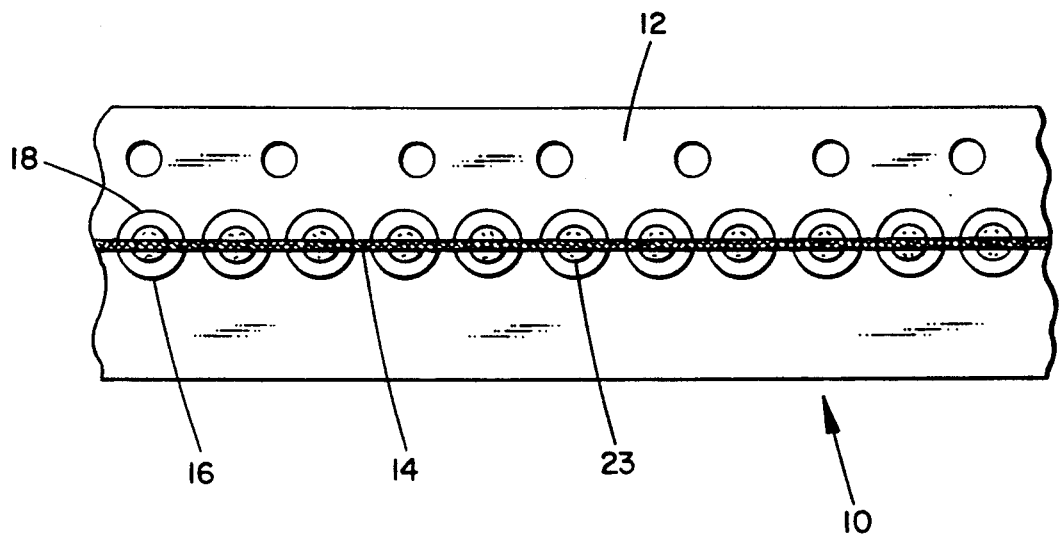
FIG. 1 is an enlarged, fragmentary view of the radiology marker system of the invention.

Referring now to the drawings, and in particular FIG. 1, the radiology marker system 10 is shown. The marker system 10 includes tape 12, which can be made of paper or another severable material, and can be coated with wax or any similar composition that allows for the release of the markers, as will be described below. Tape 12 is a single longitudinal strip. A covered wire 14 runs along the length of the tape on the side of the tape having a release-enhancing coating. The wire is manually bendable to a desired fixed position or shape, and preferably can be bent much more easily than a paper clip or similar wire. The bare wire is made of suitable material, such as a lead alloy, which is opaque to diagnostic radiation and therefore will show up on the radiographic film or image. The bare wire has a thickness that allows it to be readily severed by the user with a cutting device. Preferably, the bare wire has a thickness of 2.0 mm or less, and more preferably has a thickness of about 1 mm or less.

The wire is covered or coated with a material that will render it safe and comfortable when placed on a patient's body. Preferably, the wire is covered with a woven fabric. The covering or coating is sufficiently thick to contribute to patient comfort without substantially reducing the effectiveness of the wire as a radiological marking device. It has been found particularly useful to use covered wires that have a thickness of 2.5 mm or less, and more preferably 1.5 mm or less.

A continuous row of generally circular adhesive support pads 16 each having an adhesive side 18 which contacts the tape 12 are fastened to the wire 14. According to the preferred embodiment, the non-adhesive side 20 of the pads 16 is glued to the wire with substantially transparent glue 23. The adhesive pads 16 can be made of any suitable material, such as plastic or paper. The pads 16 may be of any size and shape appropriate to support the wire. The size and shape of the pads 16 also may depend upon whether the marker wire is used to mark spots or to outline or encircle areas of tissue. For example, when the wire is used to encircle a portion of tissue, small pads usually are preferred. Preferably, the pads 16 have a diameter of about 1 cm or less, and more preferably about 7 mm or less. In the embodiment illustrated in FIG. 2, the diameter of the pads is approximately equal to the diameter of holes made with a commercially available 3-hole punch. The radiology marker system 10 is conveniently stored in a roll 21, illustrated in phantom in FIG. 2.

Figure 2:
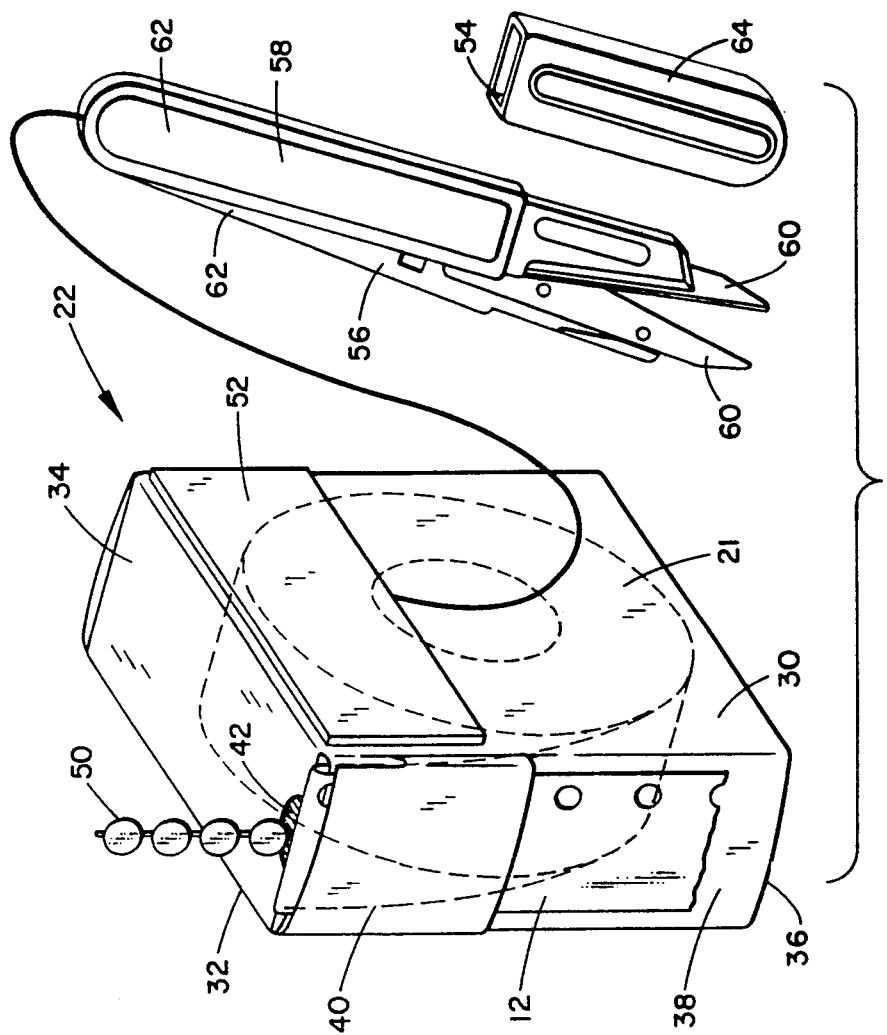
FIG. 2 is an isometric view of a dispensing container constructed in accordance with the present invention, shown from the back.
Figure 3:
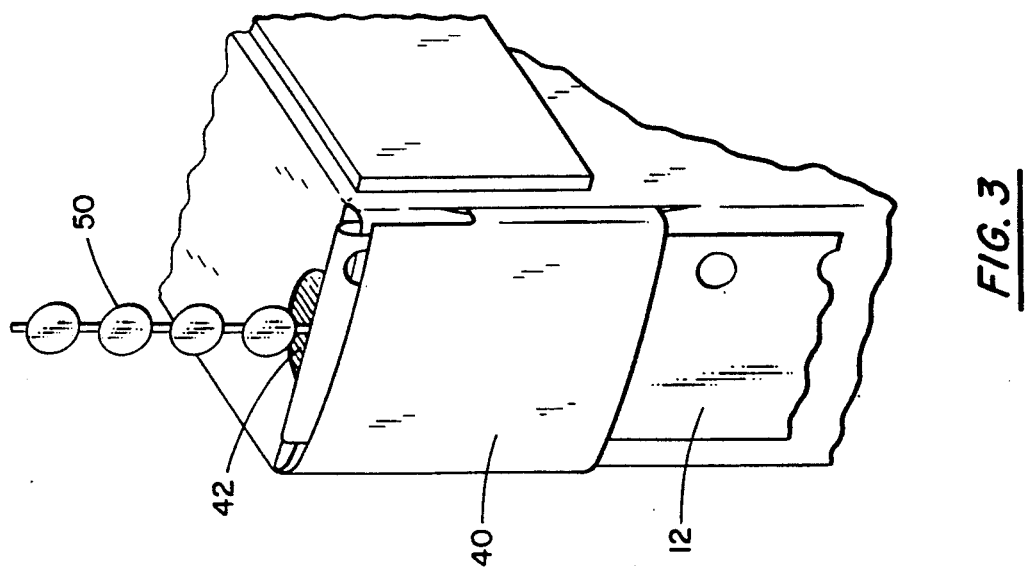
FIG. 3 is an enlarged, fragmentary view of the dispenser illustrated in FIG. 2.

Referring to FIGS. 2-3, a dispensing housing or package 22 for the radiology marker system 10 of the invention is shown. Package 22 can be constructed of any suitable material such as cardboard, heavy paper, plastic or the like and may have any shape appropriate to house roll 21, shown in phantom with dotted lines in FIG. 2. In the embodiment shown in FIG. 1, the package 22 is constructed from cardboard and folded into a generally rectangular box having wide back and front sides 30, 32, respectively. The package 22 has a narrow top dispensing side 34, an opposite, narrow bottom side 36, and a tape holding side 38 between the top dispensing side 34 and the bottom side 36 and perpendicular thereto. The package 22 further has a side flap portion 40 which overlaps the upper half of the tape holding side 38 of the package 10. The inner volume and dimensions of the package 10 are sufficient to house the roll 21 without substantially free or unoccupied space before any of the roll 21 has been dispensed. The roll 21 as shown in FIG. 2 is freely rotatable in package 10 without additional mounting means, although a journal mount or rotatable tape supply means can be included if desired.

In order to use the embodiment of the dispenser illustrated in FIG. 2, the free end 40 of tape 12 is pulled through a semicircular aperture 42 in the top end 34 of the dispensing package 22, and is looped over the tape holding side 38 of the package 10 and underneath the flap 40. As the tape 12 is pulled downward in a direction away from the top dispensing side 34, the marker 50, which is separated from the tape 12, extends vertically upward. When a sufficient length of wire has been ejected from the package 22 through aperture 42 of package 22, the wire 14 is cut and the cut marker 50 is placed on the body of a subject. The cut marker 50 can be bent to any desired shape, e.g., a circle, oval or line.

Figure 4:
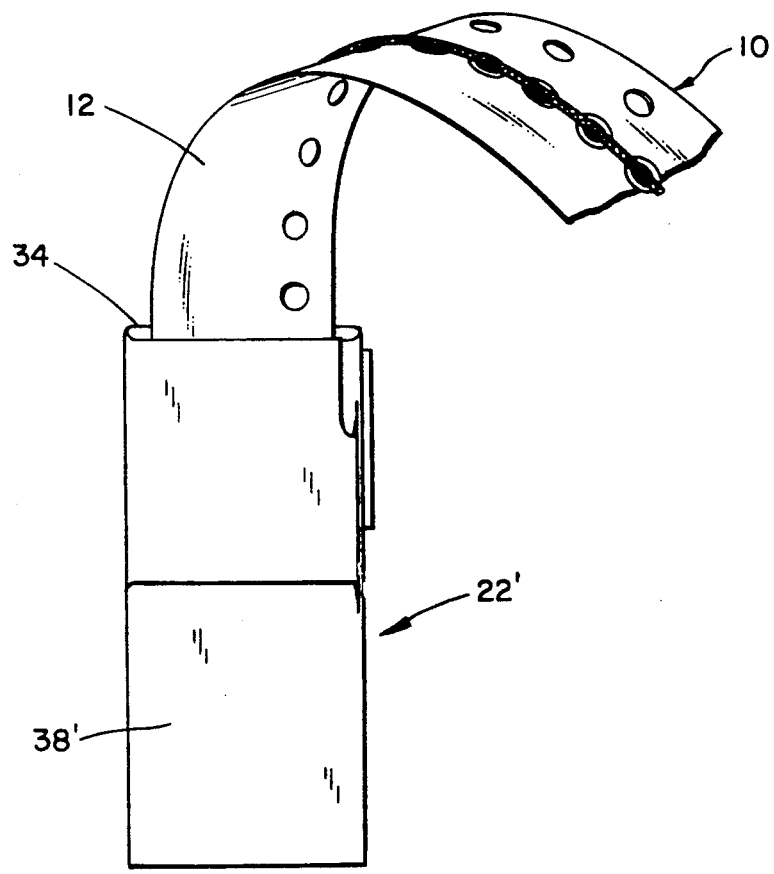
FIG. 4 is a side view of a dispenser having a second embodiment according to the invention.

FIG. 4 illustrates an alternative embodiment of the invention. In this embodiment, marker 50 remains adhered to tape 12 as tape 12 is dispensed from package 22'. Tape 12 and wire 14 then can be cut at the same time, and the marker 50 can then be removed from the base tape 12 after cutting, or tape 12 can be pulled from wire 14 and allowed to remain hanging as the wire 14 is cut. It is noted that in this embodiment of the dispenser, a flap is not needed on the side wall 38, of the package 22', as both the marker 50 and the tape 12 extend outward from the dispenser at the junction of the top dispensing side 34 and the side 38' of the package 22'.

In the embodiment illustrated in FIG. 2, package 22 has an adhesive backing 52 which is of sufficient strength to adhere package 22 to a wall or other support. The package 22 preferably further includes wire clippers 54 attached to package 10 by a piece of fabric covered wire. Clippers 54 include first and second elongated cutting members 56,58, respectively, that are pivotally connected at one end in an overlapping arrangement, and are biased away from each other at the opposite end. Each cutting member includes a metal cutting blade 60 at the end opposite to the connection, and a plastic handle 62 that partially overlaps the handle of the other cutting member. In order to cut the marker 50, the wire is placed between the cutting blades, and the handles of the first and second cutting members are pushed toward each other with the thumb and index finger of the user, causing the blades to move to an overlapped position. The clippers have a removable protective cover 64 that is similar to a ball point pen cover and is placed over the blades when they are not in use. The blades 60 are pivoted to an overlapping position in order to fit them within the cover 64.

The markers of the invention are useful for accurate localization of scars on the skin, nipples, defining the margins of a palpable mass and are useful in diagnostic radiology, mammography, and radiation treatment planning. They can be used to delineate certain spots, or to encircle particular regions of skin or other tissue. They are particularly useful for diagnostic radiology for cases in which variations in tissue density may cast artefactual images. In radiation oncology, when certain regions of the body are to be treated, the field of radiation therapy may be radiographically defined by marking the perimeter of the field to be treated.

As can be understood from the above description, a novel marker system for use in radiology and a dispensing package containing the marker system are provided which have substantial advantages over that which is currently used. The invention results in a product that is conveniently dispensed and produces markers which are of a desired length and shape. It saves time in diagnostic radiology or treatment planning, and results in an effective, comfortable, sanitary, convenient radiographic marking system.

As will be apparent to persons skilled in the art, various modifications and adaptations of the structures above described will become readily apparent without departure from the spirit and the scope of the invention, the scope of which is defined in the appended claims.

We claim:

1. A marker system for use in radiology, comprising:
   an elongated base tape having a length,
   a bendable, covered wire containing a material that is not opaque to imaging radiation, the wire extending in a direction parallel to the length of the base tape, and
   a plurality of adhesive support pads fixedly aligned along the covered wire, the adhesive pads being releasably adhered to the base tape and being manually removable from the base tape together with the wire for releasable adherence to a subject.

2. A marker system according to claim 1, wherein the wire is covered with fabric.

3. A marker system according to claim 2, wherein the wire contains lead.

4. A marker system according to claim 1, wherein the wire diameter is about 1 mm or less exclusive of the covering.

5. A marker system according to claim 4, wherein the covered wire diameter is about 2 mm or less.

6. A marker system according to claim 2, wherein the adhesive markers are round.

7. A marker system according to claim 6, wherein the adhesive pads each have a diameter of 1 cm or less.

8. A marker system according to claim 6, wherein the adhesive members have a diameter of about 7 mm or less.

9. A marker system according to claim 2, wherein the adhesive pads have adhesive on only one side.

10. A marker system according to claim 6, wherein the covered wire diameter is about 1.5 mm or less.

11. A dispensing package for markers to be used in radiology, comprising:
    tape supply means,
    an elongated base tape disposed in the supply means and dispensable therefrom, the tape having a length,
    a bendable, covered wire containing a material that is not opaque to imaging radiation, the wire extending in a direction parallel to the length of the tape, and a plurality of adhesive support pads fixedly aligned along the covered wire, the adhesive pads being releasably adhered to the base tape and being manually removable from the base tape together with the wire for releasable adherence to a subject.

12. A dispensing package according to claim 11, wherein the wire is covered with fabric.

13. A dispensing package according to claim 11, wherein the tape supply means includes a housing.

14. A dispensing package according to claim 13, wherein the housing includes an adhesive for mounting the dispensing package to a wall.

15. A dispensing package according to claim 12, wherein the wire contains lead.

16. A dispensing package according to claim 11, further comprising clippers connected to the housing.

17. A marker system for use in radiology, comprising:
an elongated base tape,
a bendable, covered wire containing a material that is not opaque to imaging radiation, the covered wire having a diameter of about 2 mm or less, and
a plurality of adhesive support pads fixedly aligned along the covered wire, the adhesive pads being releasably adhered to the base tape and being manually removable from the base tape together with the wire for releasable adherence to a subject.

18. A marker system according to claim 17, wherein the wire is covered with fabric.

19. A marker system according to claim 17, wherein the wire contains lead.

20. A marker system according to claim 18, wherein the wire contains lead.

* * * * *